(12) United States Patent
Zhang et al.

(10) Patent No.: US 9,278,948 B2
(45) Date of Patent: Mar. 8, 2016

(54) LINE LEAF INULA FLOWER LACTONE A AND METHODS FOR PREPARING AND USING THE SAME FOR TREATING MULTIPLE SCLEROSIS

(71) Applicant: SHANXI ZHENDONG PILOT BIOLOGICAL SCIENCE AND TECHNOLOGY CO., LTD., Jinzhong, Shanxi (CN)

(72) Inventors: Weidong Zhang, Shanghai (CN); Lei Shan, Shanghai (CN); Juan Su, Shanghai (CN); Huizi Jin, Shanghai (CN); Huiliang Li, Shanghai (CN); Yunheng Shen, Shanghai (CN); Xike Xu, Shanghai (CN); Runhui Liu, Shanghai (CN)

(73) Assignee: Shanxi Zhendong Pilot Biological Science And Technology Co., Ltd., Jinzhong (CN)

( * ) Notice: Subject to any disclaimer, the term of this patent is extended or adjusted under 35 U.S.C. 154(b) by 0 days.

(21) Appl. No.: 14/576,164

(22) Filed: Dec. 18, 2014

(65) Prior Publication Data
US 2015/0105458 A1    Apr. 16, 2015

Related U.S. Application Data

(63) Continuation of application No. PCT/CN2012/001411, filed on Oct. 22, 2012.

(30) Foreign Application Priority Data

Jun. 21, 2012   (CN) .......................... 2012 1 0208157

(51) Int. Cl.
| | | |
|---|---|---|
| C07D 307/00 | (2006.01) |
| C07D 307/93 | (2006.01) |
| A61K 9/19 | (2006.01) |
| A61K 31/365 | (2006.01) |
| A61K 36/28 | (2006.01) |
| A61K 9/00 | (2006.01) |
| A61K 9/20 | (2006.01) |

(52) U.S. Cl.
CPC ............ C07D 307/93 (2013.01); A61K 9/0019 (2013.01); A61K 9/19 (2013.01); A61K 9/2018 (2013.01); A61K 9/2059 (2013.01); A61K 31/365 (2013.01); A61K 36/28 (2013.01); A61K 2236/39 (2013.01)

(58) Field of Classification Search
CPC .................................................. A61K 31/365
USPC ......................................................... 549/299
See application file for complete search history.

(56) References Cited

FOREIGN PATENT DOCUMENTS
| | | |
|---|---|---|
| CN | 101830875 A | 9/2010 |
| KR | 20110087448 A | 8/2011 |

OTHER PUBLICATIONS

Nie et al. Journal of Natural Products (2010), 73(6), 1117-1120.*
Lassmann, J Neural Transm (2011) 118:747-752.*
Lee et al. Abstract of KR 2011087448, STN Accession No. 2011:980850 Document No. 155:321110.*
LeeClaim5p. 3; year 2011.*
McCarthy et al. Methods Mol Biol. 2012 ; 900: 381-401.*
U.S. Appl. No. 14/576,027, filed Dec. 18, 2014, Zhang, Weidong et al., co-pending application.
Huang, Zhigang et al., "Relationship between nitric oxide and the development of viral myocarditis in mice," Chinese Journal of Endemiology, vol. 19, No. 5, pp. 330-332, ISSN 1000-4955 (Sep. 2000).
Nie, Li-Yue et al., "Sesquiterpenoids from *Inula lineariifolia* Inhibit Nitric Oxide Production," J. Nat. Prod., vol. 73, 1117-1120 (2010).

* cited by examiner

*Primary Examiner* — Nizal Chandrakumar
(74) *Attorney, Agent, or Firm* — Manni Li; Mei & Mark LLP

(57) ABSTRACT

Preparation and application of line leaf *inula* flower lactone A in the multiple sclerosis, having a structure of

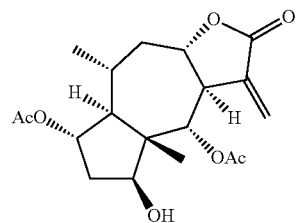

Line leaf *inula* flower lactone A has therapeutic effects on experimental autoimmune encephalomyelitis (EAE) model, and is used to develop drug for treating multiple sclerosis (MS). Line leaf *inula* flower lactone A drug is a combination containing the active ingredient of line leaf *inula* flower lactone A and conventional pharmaceutically carrier, and may be in forms of tablets, dispersible tablets, mouth collapse tablets, retard tablets, capsule, soft capsule, dropping pill, granules, injection, powder injection, or aerosol. The pharmaceutical composition is used for treating multiple sclerosis, has tremendous developing potentiality because of its high value of clinical application.

4 Claims, 2 Drawing Sheets

LINE LEAF INULA FLOWER LACTONE A AND METHODS FOR PREPARING AND USING THE SAME FOR TREATING MULTIPLE SCLEROSIS

CROSS-REFERENCE TO RELATED APPLICATIONS

The subject application is a continuation of PCT international application PCT/CN2012/001411 filed on Oct. 22, 2012, which in turn claims priority on Chinese patent applications CN 201210208157.4 filed on Jun. 21, 2012. The contents and subject matter of the PCT and Chinese priority applications are incorporated herein by reference.

TECHNICAL FIELD

The present invention relates to Chinese traditional medicine *inula* flowers, specifically, the preparation of *Inula Lineariifolia* lactone A from *inula* flowers and its application in the preparation of medicine for treating multiple sclerosis.

BACKGROUND OF THE INVENTION

Since it was first proposed in 1868 by the French doctor Charcot, multiple sclerosis (MS) has been a disease that is still extremely difficult to treat in the world. It is a chronic autoimmune disease that causes myelin destroyed in the brain, spinal cord, and optic nerve fiber layer, at last, affects the normal nerve and cause physical disabilities. Because the high recurrence rate and morbidity, the chronic course and tendency to be developed in young people, MS has become a common and serious nervous system disease. Usually, MS outbreaks reach the peak at the age of around 30, thus, it causes serious damage to people's productivity and quality of life. At the same time, it makes great burden to the government, society, and economic development.

At present, there is no specific treatment for MS clinically, neither is there satisfactory therapeutic drugs. Glucocorticoid is usually given in acute phase of MS, and interferon—γ, Glatiramer acetate, Natalizumab for the relapse—remission phase. Autologous stem cell transplantation is considered in patients with severe disease. Although hormone therapy could alleviate symptoms in acute stage, the obvious side effects limits its long-term application. Single target drugs such as IFN-β, GA and Natalizumab are not only expensive but also prone to produce resistance. The drugs mentioned above are subject to intravenous or subcutaneous injection dosage, which can not effectively improve MS relapse and demyelinating fundamental problems. Therefore, oral drugs that effective control MS is of great significance. Traditional Chinese medicines have the characteristics of multiple targets and the action of system adjustment, which show certain medication advantages in treating complexity and refractory diseases such as MS.

The line leaf *inula* flower (*Inula lineariifolia* Turcz. (syn. *Inula linariaefolia*)) is a perennial herb that belongs to the family of Asteracece and the genus of *Inula*, and has the common names of narrow-leaf *inula* flower, long-leaf *inula* flower, and small *inula* flower. They widely grow in the northeast, north, central, and eastern China, such as Henan, Hebei, and other provinces, and in Mongolia, North Korea, far east Russia, and Japan. It commonly grows in hills, wasteland, road, river, etc. Chinese traditional medicine *inula* flowers are the capitulum of the *inula* flowers or big flower *inula* flowers, and the entire herbal plant (gold boiling grass) may be used for medicinal purpose. Line leaf *inula* flowers have been used as the *inula* flowers in east China and other parts of China, and has been used for ventilation, diuresis, anti-inflammatory, softening hard masses, etc., and recorded in the Chinese Pharmacopoeia (1963 edition); however, line leaf *inula* flowers have ceased to be used as a medicine, as the patient, after being served, has the reactions of nausea, vomiting, etc.

SUMMARY OF THE INVENTION

The chemical composition of line leaf *inula* flowers has been investigated and a large number of sesquiterpenoids have been isolated by inventors for the subject application. Related researches have been published (Li-Yue Nie et al., "Sesquiterpenoids from *Inula lineariifolia* inhibit nitric Oxide production," Journal of Natural Products, 2010, 73(6): 1117-1120). The line leaf *inula* flower lactone A has been applied in preparing anti-inflammatory drugs (See related Chinese Patent Application No. 201010200697.9). Further studies have found that line leaf *inula* flower lactone A shows therapeutic effects on multiple sclerosis and is useful for developing novel medicine.

The present invention provides methods for extracting line leaf *inula* flower lactone A from line leaf *inula* flowers and applying it in preparing multiple sclerosis treatment medicine.

The present invention provides a line leaf *inula* flower lactone A as a drug for treating multiple sclerosis, and the line leaf *inula* flower lactone A has the following structure:

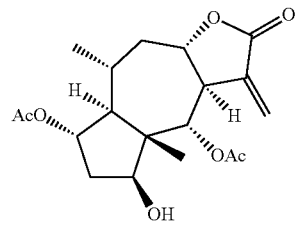 [SMILES: C=C1C(=O)O[C@H]2C[C@@H](C)[C@@H]3[C@@H](OC(C)=O)C[C@H](O)[C@@]3(C)[C@@H](OC(C)=O)[C@H]12]

Line leaf *inula* flower lactone A of the present invention is obtained as follows:

Dried line leaf *inula* flower grass is cut into pieces and extracted with 8~20 times (W/W) of 80~95% ethanol for 1 to 3 times, and each extraction lasts for 2 to 3 hours. The extracted solution from each extraction are combined and condensed into a liquid extract under the reduced pressure, and the liquid extract contains an equivalent of about 0.8 g to 1.2 g line leaf *Inula* flowers in 1 ml liquid extract. Water is added to dilute the liquid extract, and the amount of water added is 1 to 3 times the weight of the liquid extract. Then, the diluted liquid extract is extracted with 0.5 to 2 times (V/V) petroleum ether for 3 to 5 times, and the petroleum ether layer is obtained. The petroleum ether layer runs on a silica gel column chromatography, and is washed with 100:0 to 1:1 (V/V) petroleum ether/ethyl acetate gradient elution to separate the ingredients. After a thin-layer chromatography detection, an elution containing line leaf *inula* flower lactone A is collected, and run on a C18 reverse phase chromatography and washed with 50:100 to 70:100 (W/W) methanol/water gradient elution to purify. A thin-layer chromatography test confirms that a purified line leaf *inula* flower lactone A is obtained.

Experimental autoimmune encephalomyelitis (EAE) is a well established animal model that is also the most widely accepted animal model of multiple sclerosis (MS) for the study of the underlying pathogenesis and serves as a valuable tool for testing new therapies of MS. Line leaf *inula* flower lactone A shows good treatment effect on EAE, and it may be used for the preparation of a drug for the treatment of multiple sclerosis.

The present invention provides a pharmaceutical composition having line leaf *inula* flower lactone A as the active ingredient in combination with a conventional pharmaceutical carrier. The pharmaceutical composition may be in the form of tablets, dispersible tablets, mouth collapse tablets, retard tablets, capsule, soft capsule, dropping pill, granules, injection, powder injection, or aerosol, etc. The present invention provides a new drug for the treatment of multiple sclerosis. It has tremendous developing potentiality because of its high value of clinical application.

DETAILED DESCRIPTION OF THE INVENTION

Figure 1:
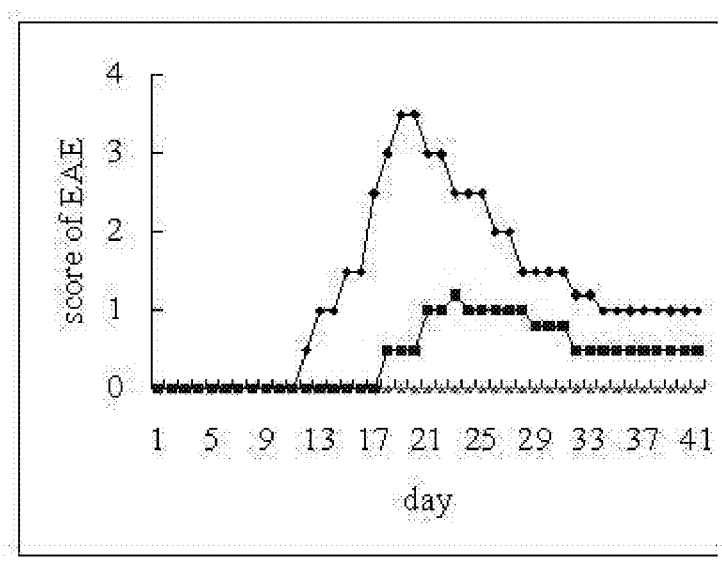
FIG. 1 shows the effects of line leaf *inula* flower lactone A on EAE mice (intragastric administration dose: 50 mg/kg). Top line: Line leaf *inula* flower lactone A group; Middle line: EAE model group; Bottom line: blank group.

The following examples further describe the present invention in details but do not limit the scope of the present invention. One of ordinary skill in the art knows how to make modifications based on the examples without departing from the scope of the present invention.

Example 1

Preparation of Line Leaf *Inula* Flower Lactone A

Dried Line leaf *inula* flower grass 50 kg was cut into pieces, then extracted with 750 L ethanol (80~95% V/V) for two times, 2 hours each time. The extracts from each extraction were merged and under reduced pressure condensed into a liquid extract. The liquid extract contained the equivalent of 1 g line leaf *inula* flowers per milliliter. Water 750 L was added to diluted the liquid extract, then extracted 5 times with 50 L petroleum ether to get the petroleum ether layer. Volume at 100:0~1:1 petroleum ether/ethyl acetate gradient elution was used on silica gel column chromatography to separated the samples, thin-layer chromatography detection, collected the elution which contained line leaf *inula* flower lactone A. Weight for 50:100~70:100 methanol/water gradient elution was used to purify the extracts on C18 reverse phase chromatography, and a thin-layer chromatography test to get 45.3 g line leaf *inula* flower lactone A as the single product.

The obtained compound was tested by mass spectrometry to determine that the molecular weight was 366, and the molecular formula was $C_{19}H_{28}O_7$. Then, its carbon spectrum, hydrogen spectrum, and two-dimensional spectral data were obtained through the hydrogen nuclear magnetic resonance (NMR) analysis. The structural analysis was performed and it conformed with the data of the compound Line leaf *Inula* flowers lactone A.)

Example 2

Pharmacodynamics Studies of Line Leaves *Inula* Flowers Lactone A on EAE Model

Mice with experimental autoimmune encephalomyelitis (EAE) model is an ideal animal model for human multiple sclerosis (MS), often used in the study of the mechanism of immune activation and immunosuppression.

2.1. EAE Model

EAE was induced in C57BL/6 mice (six mice per group) by subcutaneous injection of 0.1 ml of $MOG_{33-55}$ (in PBS, 300 μg/per mouse) on day 0, emulsified with Complete Freund's adjuvant (1:1) supplemented with Mycobacterium tuberculosis H37Ra antigen (400 μg/per mouse) or with Complete Freund's adjuvant alone as a control. All mice immunized with MOG received 250 ng pertussis toxin prepared in PBS, on days 0 and 2 by intraperitoneal injection.

2.2. Treatment of Line Leaf *Inula* Flower Lactone A on EAE Mice

Line leaf *inula* flower lactone A 45.3 g (from Example 1) was suspended in 0.5% CMC—Na (carboxymethyl cellulose sodium) to make a mixture with final concentration as 10 mg/ml, then diluted to four concentration gradients: (1) 25 mg/kg per day; (2) 50 mg/kg per day; (3) 100 mg/kg per day; (4) 200 mg/kg per day. The drug was given to the mice by intragastric administration from day 0 to day 30.

2.3. Results

Figure 2:
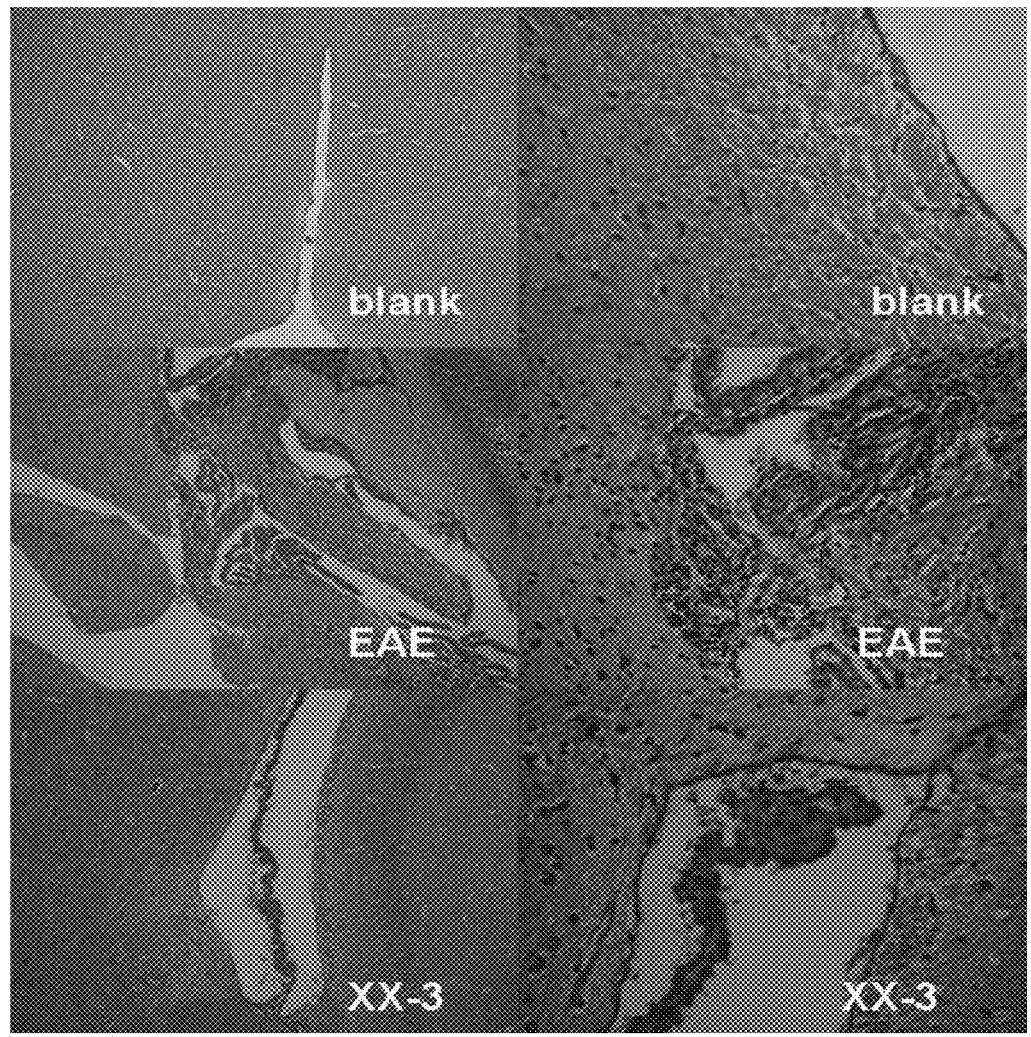
FIG. 2 shows the effects of line leaf *inula* flower lactone A on the brain tissue of EAE mice by HE staining (intragastric administration: 50 mg/kg).

Intragastric administration of line leaf *inula* flower lactone A conducted at 50 mg/kg, once per day (50 mg/kg) and higher doses could significantly delay the onset of EAE and reduced the severity of the disease as shown in FIG. 1. Mice in the EAE model group showed inflammation cells infiltration in brain and blood vessels, the arrangement of the organization was loose, and the edge was not clear. Mice in the line leaf *inula* flower lactone A treated groups of 50 mg/kg and higher doses showed reduced number of inflammatory cells in brain and blood vessels, the arrangement of the organization basically returned to normal condition as shown in FIG. 2.

The experiment was repeated 3 times, and results were the same as mentioned above.

2.4. Toxicity.

No obvious toxic reaction was observed after treating the mice with 200 mg/kg by intragastric administration once per day for a month.

2.5. Conclusion:

Treated EAE mice with line leaf *inula* flower lactone A (50-200 mg/kg, intragastric administration) could decrease inflammation and delay disease onset and disease severity significantly. Line leaf *inula* flower lactone A could be potentially important for anti-MS drug development and application to multiple sclerosis therapy.

Example 3

Tablet Preparation

Line leaf *inula* flower lactone A 25 g, lactose 210 g, and corn starch 60 g were mixed to form a uniform water wet mixture, sifted after wetting and drying, and sieved. Magnesium stearate 5 g was added and the mixture was made into tablets, with each piece containing 300 mg line leaf *inula* flower lactone A 25 mg.

Example 4

Injection Preparation

Line leaf *inula* flower lactone A 5 g and glucose 50 g were dissolved in a suitable amount of water for injection to obtain a solution. The solution was filtered and bottled under aseptic conditions into the infusion bottle at 100 ml per bottle. Each bottle contained line leaf *inula* flower lactone A 5 mg.

Example 5

Freeze-Dried Powdery Preparation for Injection

Line leaf *inula* flower lactone A 10 g and mannitol 30 g were dissolved in suitable amount of injection water and filtered to obtain a solution. The solution was bottled under aseptic conditions in Schering bottles (10 ml Schering bottles, at 2 ml per bottle) and freeze-dried. Each bottle contained line leaf *inula* flower lactone A 10 mg.

We claim:

1. A method of treating multiple sclerosis comprising administering a therapeutically effective amount of a pharmaceutical composition comprising an isolated and purified line leaf *inula* flower lactone A having a structure of

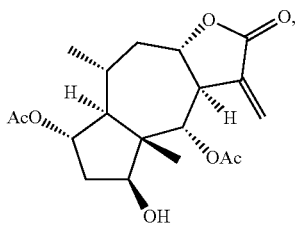 [SMILES: C=C1C(=O)O[C@H]2C[C@@H](C)[C@@H]3[C@@H](OC(C)=O)C[C@H](O)[C@@]3(C)[C@@H](OC(C)=O)[C@H]12]

wherein the amount of the isolated and purified line leaf *inula* flower lactone A in the pharmaceutical composition is about 50 mg to 200 mg per kilogram of weight of a subject to be treated for multiple sclerosis.

2. The method according to claim 1 wherein the line leaf *inula* flower lactone A is a sole active ingredient in the composition.

3. The method according to claim 1, wherein the pharmaceutical composition is in a form of tablets, dispersible tablets, mouth collapse tablets, retard tablets, capsule, soft capsule, dropping pill, granules, injection, powder injection, or aerosol.

4. The method for treating multiple sclerosis according to claim 1, wherein the pharmaceutical composition is administered by intraperitoneal injection or intragastric administration.

* * * * *